(12) United States Patent
Oba et al.

(10) Patent No.: US 9,482,637 B2
(45) Date of Patent: Nov. 1, 2016

(54) SENSOR

(71) Applicant: NGK SPARK PLUG CO., LTD., Nagoya-shi, Aichi (JP)

(72) Inventors: Takehiro Oba, Konan (JP); Yuichi Yamada, Komaki (JP); Shingo Ito, Ichinomiya (JP); Shogo Nagata, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 379 days.

(21) Appl. No.: 14/246,530

(22) Filed: Apr. 7, 2014

(65) Prior Publication Data

US 2014/0299469 A1    Oct. 9, 2014

(30) Foreign Application Priority Data

Apr. 8, 2013 (JP) ................. 2013-080275
Jan. 9, 2014 (JP) ................. 2014-002211

(51) Int. Cl.

| | | |
|---|---|---|
| *G01N 27/26* | (2006.01) | |
| *G01N 7/00* | (2006.01) | |
| *G01N 21/00* | (2006.01) | |
| *G01N 27/00* | (2006.01) | |
| *G01N 31/00* | (2006.01) | |
| *G01N 33/00* | (2006.01) | |
| *G01N 27/407* | (2006.01) | |

(52) U.S. Cl.
CPC ................. *G01N 27/407* (2013.01)

(58) Field of Classification Search
CPC ........ G01N 27/26; G01N 7/00; G01N 21/00; G01N 27/00; G01N 31/00; G01N 33/00

USPC ........... 422/83, 98; 204/427, 428, 424, 412, 204/431, 432; 29/592, 592.1; 73/114.69, 73/114.71, 114.72, 23, 2, 32

See application file for complete search history.

(56) References Cited

U.S. PATENT DOCUMENTS

| | | | | |
|---|---|---|---|---|
| 4,155,827 | A * | 5/1979 | Maurer et al. ................. | 204/428 |
| 4,556,475 | A * | 12/1985 | Bayha et al. ................. | 204/427 |
| 4,636,293 | A * | 1/1987 | Bayha et al. ................. | 204/428 |
| 4,750,256 | A * | 6/1988 | Wertheimer et al. ........ | 29/25.03 |
| 6,231,348 | B1 | 5/2001 | Mayer et al. | |
| 7,032,433 | B2 * | 4/2006 | Hayashi et al. ............. | 73/31.05 |

(Continued)

FOREIGN PATENT DOCUMENTS

| | | |
|---|---|---|
| JP | 2000-500876 A | 1/2000 |
| JP | 2005-91223 A | 4/2005 |
| JP | 2009-216388 A | 9/2009 |

*Primary Examiner* — Brian J Sines
(74) *Attorney, Agent, or Firm* — Sughrue Mion, PLLC

(57) ABSTRACT

A sensor including: a detection element; terminal members; and a separator, wherein at least one specific first electrode terminal portion and an other first electrode terminal portion are formed on a first main surface of the detection element, wherein a second electrode terminal portion formed on a second main surface of the detection element is disposed so as to be offset from the specific first electrode terminal portion and to overlap with the other first electrode terminal portion in the axial direction, and in a thickness direction, a distance between the detection element and a specific first frame body portion brought into electrical connection with the specific first electrode terminal portion is larger than a distance between the detection element and the other first frame body portion brought into electrical connection with the other first electrode portion.

6 Claims, 12 Drawing Sheets

(56) References Cited

U.S. PATENT DOCUMENTS

| | | | |
|---|---|---|---|
| 7,340,942 B2* | 3/2008 | Matsuo et al. | 73/31.05 |
| 7,424,819 B2* | 9/2008 | Fujita et al. | 73/31.05 |
| 7,568,378 B2* | 8/2009 | Yoshikawa et al. | 73/31.05 |
| 8,105,470 B2 | 1/2012 | Matsui et al. | |
| 8,191,414 B2* | 6/2012 | Kume et al. | 73/114.73 |
| 8,398,837 B2 | 3/2013 | Matsui et al. | |
| 9,201,040 B2* | 12/2015 | Yamada et al. | |
| 2006/0237315 A1* | 10/2006 | Matsuo et al. | 204/424 |
| 2006/0288759 A1* | 12/2006 | Okumura et al. | 73/31.05 |
| 2009/0223818 A1 | 9/2009 | Matsui et al. | |
| 2010/0139364 A1* | 6/2010 | Kume et al. | 73/23.31 |
| 2012/0097537 A1 | 4/2012 | Matsui et al. | |

* cited by examiner

SENSOR

This application is based on Japanese Patent Application No. 2013-080275, filed Apr. 8, 2013, and Japanese Patent Application No. 2014-002211, filed Jan. 9, 2014, incorporated herein by reference in its entirety.

TECHNICAL FIELD

The present invention relates to a sensor such as a gas sensor, a temperature sensor and the like.

BACKGROUND ART

Patent Document 1 discloses a sensor which includes a plate-like detection element which extends in an axial direction of the sensor as a gas sensor, a temperature sensor or the like. A plurality of electrode terminal portions are formed on each of two main surfaces (opposing surfaces, which extend along the axial direction) of a rear end portion of the detection element. Terminal members are in elastic contact with the corresponding electrode terminal portions, whereby the electrode terminal portions are electrically connected to an external circuitry via these terminal members.

Three electrode terminal portions are provided on each of the two main surfaces of the detection element shown in FIG. 2 of Patent Document 1. However, one electrode terminal portion which lies in the middle of the three electrode terminal portions is disposed in a position where the one electrode terminal portion is offset rearwards in the axial direction from the other two electrode portions which lie on both sides thereof. This type of arrangement of electrode terminal portions in which one is offset from the remaining electrode terminal portions in the axial direction is made use of in, for example, ensuring an insulation distance between the electric terminal portions when attempting to produce a small sized detection element. Namely, since the width of the main surface of the detection element is reduced when attempting to reduce the size of the detection element, in the event that a plurality of electrode terminal portions are disposed on the main surface so as to align them in a width direction thereof, a distance between the electrode terminal portions becomes excessively small, resulting in the possibility that sufficient insulation cannot be ensured. Here, by offsetting a portion of the plurality of electrode terminal portions in the axial direction, it becomes possible to ensure sufficient distances among the electrode terminal portions.

PRIOR ART DOCUMENT

[Patent Document 1] Japanese Patent Application Laid-Open (kokai) No. 2009-216388

SUMMARY OF THE INVENTION

Problem to be Solved by the Invention

Incidentally, as shown in FIG. 13 of Patent Document 1, among sensors, there exists a type of sensor in which the number of (for example, three) electrode terminal portions which are provided on one main surface of a detection element is different from the number of (for example, two) electrode terminal portions which are provided on the other main surface. In the event that the arrangement of electrode terminal portions in which one is offset from the remaining electrode terminal portions in the axial direction is adopted for this type of sensor, a problem is likely to be caused when inserting the plurality of electrode terminal portions into a rear end of the detection element when assembling the sensor. Specifically, in the event that one of the electrode terminal portions which are provided on the one main surface is disposed so as to be offset from the others in the axial direction, the other electrode terminal portions provided on the one main surface is positioned so as to overlap with the electrode terminal portions which are provided on the other main surface. On the other hand, the electrode terminal portion which is disposed to be offset in the way described above is positioned so as to be offset from the electrode terminal portions provided on the other main surface in the axial direction. Since the plurality of terminal members are in contact with the electrode terminal portions by making use of the spring properties (elasticity) of the plate materials thereof, forces exerted on the detection element from the terminal members via the electrode terminal portions which are disposed so as to overlap with each other (the other electrode terminal portions and the electrode terminal portions provided on the other main surface) are almost balanced against each other. However, the balance of the forces exerted on the detection element from the terminal members via all the electrode terminal portions is lost by a force exerted on the detection element from the terminal member via the electrode terminal portion which is offset in the axial direction. Then, in the event that the degree of the imbalance of the forces exerted on the detection element becomes too large, there is a possibility that a sufficient electric connection cannot be ensured between part of the plurality of electrode terminal portions and a part of the plurality of terminal members. In particular, when inserting the plurality of terminal members into the rear end of the detection element, in the event that the balance between the forces exerted on the two main surfaces of the detection element is impaired excessively, the detection element is inclined, and as a result, there is caused a problem that the complete electrical contact between part of the plurality of electrode terminal portions and the part of the plurality of terminal members is lost.

Means for Solving the Problem

The invention has been made with a view of solving the problem, which can be realized by the following aspects of the invention.

(1) A mode of the present invention provides a sensor including a detection element extending along an axial direction, and having a first main surface and a second main surface which face opposite each other and constitute a portion of a surface extending along the axial direction, and a plurality of electrode terminal portions disposed on each of the first main surface and the second main surface; a plurality of terminal members provided in correspondence with the electrode terminal portions and electrically connected to the corresponding electrode terminal portions, each of the terminal members comprising an elongated frame body portion extending along the axial direction, a folded portion connecting with a forward end side of the frame body portion and folded back towards a detection element side and a rearward end side, and an element contact portion connecting with the folded portion at a forward end side thereof and brought into elastic contact with the electrode terminal portion; and a separator surrounding the element contact portions and a portion of the detection element at which the plurality of electrode terminal portions are disposed, wherein, with a direction in which the first main surface and the second main surface face opposite each other being defined as a thickness direction, a plurality of first electrode terminal portions are formed on the first main surface of the detection element, the plurality of first electrode terminal portions including at least one specific first electrode terminal portion and an other first electrode terminal portion other than the specific first electrode terminal portion, and the specific first electrode terminal portion and the other first electrode terminal portion being disposed so as be offset from each other in the axial direction of the detection element, a plurality of second electrode terminal portions are formed on the second main surface of the detection element, the second electrode terminal portion is disposed so as to overlap with the other first electrode terminal portion in the axial direction of the detection element and is disposed so as to be offset from the specific first electrode terminal portion in the axial direction of the detection element, and in the frame body portions of the terminal members, with respect to the thickness direction of the detection element, a distance between the detection element and a specific first frame body portion, which is brought into electrical connection with the specific first electrode terminal portion on the first main surface, is larger than a distance between the detection element and the other first frame body portion, which is brought into electrical connection with the other first electrode portion.

According to this sensor, the distance between the detection element and the specific first frame body portion is larger than the distance between the detection element and the other first frame body portion. Therefore, the force exerted on the specific first electrode terminal portion from the terminal member which has the specific first frame body portion becomes weaker than the force exerted on the other first electrode terminal portion from the terminal member which has the other first frame body portion. Namely, in the first electrode terminal portions which are provided on the first main surface, even though the specific first electrode terminal portion is disposed so as to be offset from the other first electrode terminal portion in the axial direction and is disposed so as to be offset from the second electrode terminal portions provided on the second main surface in the axial direction, the force exerted on the specific first electrode terminal portion from the terminal member which has the specific first frame body portion is reduced, whereby the force exerted to the other first electrode terminal portion from the other first frame body portion and the force exerted on the second electrode terminal portion from the terminal member affect the force exerted to the detection element from the whole of the terminal members. As a result, it is possible to mitigate the influence imposed by the problem that the balance of the forces exerted on the two main surfaces of the detection element is impaired excessively to thereby make incomplete the electrical connection between a part of the electrode terminal portions and a part of the terminal members.

(2) The sensor of the above-mentioned may be such that, in the frame body portions of the terminal members, with respect to the thickness direction of the detection element, a distance between the detection element and a second frame body portion, which is brought into electrical contact with the second electrode terminal portion, is the same as the distance between the detection element and the other first frame body portion.

According to this sensor, the force exerted individually on the other first electrode terminal portion from the terminal member which is brought into contact with the other first electrode terminal portion and the force exerted individually on the second electrode terminal portion from the terminal member which is brought into contact with the second electrode terminal portion can be made almost the same, whereby the force exerted on the detection element from the whole of the terminal members tends to be well balanced easily. As a result, it is possible to mitigate further the influence imposed by the problem that the balance of the forces exerted on the two main surfaces of the detection element is impaired excessively to thereby make incomplete the electrical connection between a part of the electrode terminal portions and a part of the terminal members.

(3) The sensor of the above-mentioned may be such that, with a direction which is along the first main surface and the second main surface and which is orthogonal to the axial direction being defined as a width direction, the other first electrode terminal portion and the second electrode terminal portion are disposed so as to overlap with each other in the width direction.

According to this sensor, the force exerted individually on the other first electrode terminal portion from the terminal members which is brought into contact with the other first electrode terminal portion and the force exerted individually on the second electrode terminal portion from the terminal member which is brought into contact with the second electrode terminal portion are symmetrical with each other across the detection element also in the width direction, whereby the force exerted on the detection element from the whole of the terminal members tends to be better balanced easily. As a result, it is possible to mitigate further the influence imposed by the problem that the balance of the forces exerted on the two main surfaces of the detection element is impaired excessively to thereby make incomplete the electrical connection between a part of the electrode terminal portions and a part of the terminal members.

(4) The sensor of the above-mentioned may be such that, a number of the first electrode terminal portions is larger than a number of the second electrode terminal portions.

According to this sensor, even with a sensor in which the number of the first electrode terminal portions and the number of second electrode terminal portions differ, by adopting the invention, it is possible to mitigate further the influence imposed by the problem that the balance of the forces exerted on the two main surfaces of the detection element is impaired excessively to thereby make incomplete the electrical connection between part of the electrode terminal portions and part of the terminal members.

(5) The sensor of the above-mentioned may be such that, with respect to the thickness direction of the detection element, a distance between the specific first frame body portion and the other first frame body portion is from 0.2 mm to 5 mm.

(6) The sensor of the above-mentioned may be such that, with respect to the axial direction, a distance between a contact portion between the specific first electrode terminal portion and the specific first frame body portion and a contact portion between the other first electrode terminal portion and the other first frame body portion is from 0.2 mm to 10 mm.

The present invention can be embodied in various forms other than a sensor and a terminal member. For example, the invention can be embodied in a method of manufacturing a sensor and a method of manufacturing a terminal member.

MODES FOR CARRYING OUT THE INVENTION

A. First Embodiment

A-1. Configuration of Sensor

Figure 1:
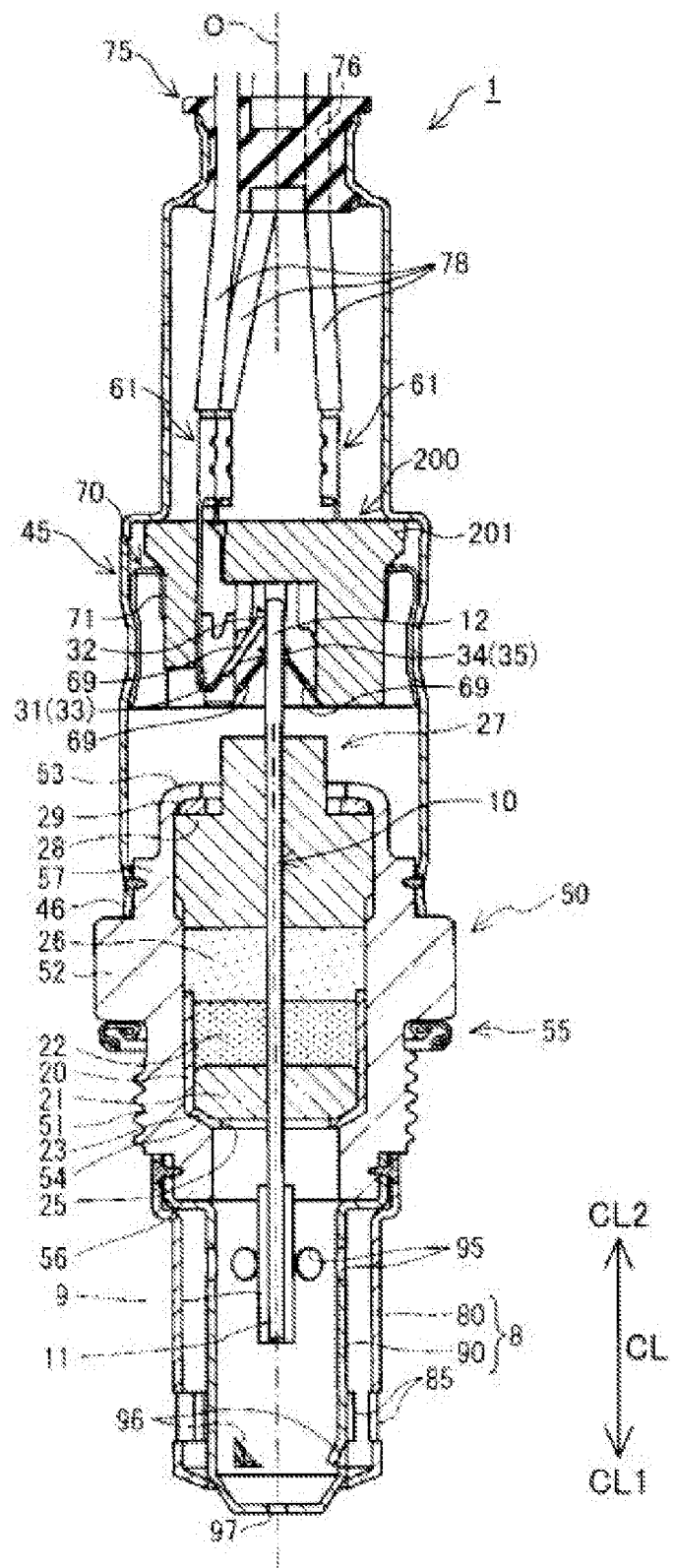
[FIG. 1] Sectional view of a gas sensor according to a first embodiment of the present invention.

FIG. 1 is a sectional view of a gas sensor 1 (corresponding to a "sensor" in the appended claims) according to a first embodiment of the present invention. In FIG. 1, an axial direction CL of the gas sensor 1, which is a direction along the axis O of the gas sensor 1, corresponds to the vertical direction. In the following description, a side toward a forward end portion 11 of a detection element 10 held in the interior of the gas sensor 1 is referred to as a forward side CL1 of the gas sensor 1, and a side toward a rear end portion 12 is referred to as a rear side CL2 of the gas sensor 1.

The gas sensor 1 shown in FIG. 1 is attached to an exhaust pipe (not shown) of an automobile. The gas sensor 1 is attached such that the forward end portion 11 of the detection element 10 held therein is exposed to exhaust gas which flows through the exhaust pipe. By means of exposure of the forward end portion 11 to exhaust gas, the gas sensor 1 detects the air/fuel ratio of exhaust gas on the basis of oxygen concentration in the exhaust gas. That is, the gas sensor 1 is a so-called full range air/fuel ratio sensor.

The detection element 10 assumes a plate-like form extending along the axial direction CL. The left-right direction on paper on which FIG. 1 appears corresponds to the thickness direction of the detection element 10, and the far side-near side direction with respect to paper on which FIG. 1 appears corresponds to the width direction of the detection element 10. The gas sensor 1 has a structure in which the detection element 10 is held in a metallic shell 50 used for attachment to an exhaust gas (not shown) of an automobile, by holding the detection element 10 in a cup 20 and supporting the cup 20 in the metallic shell 50.

The cup 20 is formed of metal and assumes a closed-bottomed tubular form. The cup 20 is a holding member for holding the detection element 10 in the metallic shell 50, and the detection element 10 is held while extending through an opening 25 formed in the bottom of the cup 20. The forward end portion 11 of the detection element 10 protrudes from the opening 25 toward the forward side CL1. The forward end portion 11 functions as a detection portion for detecting an oxygen gas component in exhaust gas. A detection portion protection layer 9 covers the outer surface of the forward end portion 11 for protecting the forward end portion 11 from poisoning by exhaust gas.

A forward-end peripheral portion 23 is a peripheral portion of the bottom of the cup 20 and is tapered. The cup 20 accommodates a ceramic ring 21 made of alumina and a talc ring 22 formed through compression of talc powder such that the detection element 10 extends through the ceramic ring 21 and the talc ring 22. The talc ring 22 is accommodated in the cup 20 in a crushed condition. In this manner, the detection element 10 is positioned and held in the cup 20.

The detection element 10 united with the cup 20 is held while being surrounded by the tubular metallic shell 50. The metallic shell 50 is formed of low-carbon steel such as SUS430. The metallic shell 50 has an externally threaded portion 51 formed on its outer circumference at a position located toward the forward end and used for attachment to an exhaust pipe. The metallic shell 50 has a forward-end engagement portion 56 which is formed on the forward side CL1 with respect to the externally threaded portion 51 and with which a protector 8 to be described later is engaged. The metallic shell 50 has a tool engagement portion 52 which is formed at a central portion with respect to the axial direction CL and with which an attaching tool is engaged. A gasket 55 is fitted to the metallic shell 50 between the forward end surface of the tool engagement portion 52 and the rear end of the externally threaded portion 51 for preventing gas leakage after attachment to the exhaust pipe. The metallic shell 50 has a rear-end engagement portion 57 which is formed on the rear side with respect to the tool engagement portion 52 and with which a tubular housing 45 to be described later is engaged, as well as a crimped portion 53 which is formed on the rear side with respect to the rear-end engagement portion 57 and holds the detection element 10 in the metallic shell 50 through crimping.

The metallic shell 50 has a stepped portion 54 formed on the inner circumference at a position substantially corresponding to the externally threaded portion 51. The forward-end peripheral portion 23 of the cup 20 is seated on the stepped portion 54. Furthermore, a talc ring 26 is inserted into the metallic shell 50 from the rear side of the cup 20 with the detection element 10 extending therethrough and is disposed in an accommodating space defined by the cup 20 and the metallic shell 50. A tubular sleeve 27 is fitted into the metallic shell 50 in such a manner as to press the talc ring 26 from the rear side. The sleeve 27 has a shoulder portion 28 formed in a stepped form on the outer circumference at a position located toward its rear end. An annular crimp packing 29 is disposed on the shoulder portion 28. In this condition, the crimped portion 53 of the metallic shell 50 is crimped so as to press forward the shoulder portion 28 of the sleeve 27 through the crimp packing 29. The talc ring 26 is crushed in the metallic shell 50 by the sleeve 27, thereby filling the accommodating space. By means of the talc ring 26 and the talc ring 22, which is charged beforehand, the cup 20 and the detection element 10 are positioned and held in the metallic shell 50.

The forward end portion 11 of the detection element 10 protrudes toward the forward side CL1 from the forward end (forward-end engagement portion 56) of the metallic shell 50. The protector 8 is attached to the forward-end engagement portion 56. The protector 8 protects the forward end portion 11 of the detection element 10 from fouling of deposits (poisoning substances such as fuel ash and oil) contained in exhaust gas, breakage caused by adhesion of water contained in exhaust gas, etc. The protector 8 has a dual structure consisting of an inner protector 90 which assumes a closed-bottomed tubular form and has inner introduction holes 95, and a tubular outer protector 80 which radially surrounds the inner protector 90 with a gap formed between the outer protector 80 and the outer circumferential surface of the inner protector 90 and has outer introduction holes 85.

Exhaust gas introduced from the outer introduction holes 85 into the gap between the outer protector 80 and the inner protector 90 swirls around the outer circumference of the inner protector 90 and is separated into gas and water. The gas is introduced into the inner protector 90 from the inner introduction holes 95, comes into contact with the detection element 10, and is then discharged from a discharge hole 97 to the outside. Meanwhile, water enters the inner protector 90 from drain holes 96 and is then discharged from the discharge hole 97 to the outside. By virtue of such constitution, the forward end portion 11 of the detection element 10 is protected from fouling of deposits contained in exhaust gas, breakage caused by thermal shock stemming from adhesion of water, etc.

Meanwhile, the rear end portion 12 of the detection element 10 protrudes toward the rear side CL2 from the rear end (crimped portion 53) of the metallic shell 50. Five electrode terminals 31 to 35 (see FIG. 2) formed of platinum (Pt) are formed on the rear end portion 12 of the detection element 10 for outward connection. Terminal members 61 are provided in correspondence with electrode terminals 31 to 35 and are in elastic contact with the electrode terminals 31 to 35, respectively. More specifically, element contact portions 69 of the terminal members 61 are in elastic contact with the corresponding electrode terminals 31 to 35. Five terminal members 61 are provided in correspondence with the five electrode terminals 31 to 35 (FIG. 1 shows only three of them). As will be described later, the present embodiment uses three types of the terminal members 61 which differ in shape. When a distinction between the three types of the terminal members 61 is required, the terms "first-type terminal member 61A," "second-type terminal member 61B," and "third-type terminal member 61C" are used. They may be called merely "terminal member 61A," "terminal member 61B," and "terminal member 61C." Also, the element contact portion 69 may be called as follows: the element contact portion of the first-type terminal member 61A may be called "element contact portion 69A;" the element contact portion of the second-type terminal member 61B may be called "element contact portion 69B;" and the element contact portion of the third-type terminal member 61C may be called "element contact portion 69C."

The gas sensor 1 further includes a tubular separator 200. The separator 200 is formed of electrically insulating ceramic. The separator 200 surrounds the rear end portion 12 of the detection element 10 and the element contact portions 69. That is, the separator 200 is disposed radially outward of the rear end portion 12 and the element contact portions 69.

The five terminal members 61 are disposed between the detection element 10 and the separator 200. The five terminal members 61 are electrically connected, at their rear ends, to a corresponding lead wire 78 among the five lead wires 78 (FIG. 1 shows three of them), respectively. This connection establishes current paths for current which flows between the electrode terminals 31 to 35 and external apparatus to which the lead wires 78 are connected.

The tubular housing 45 is attached to the rear side of the metallic shell 50. The tubular housing 45 is formed by forming stainless steel (e.g., SUS304) into a tubular shape. The tubular housing 45 surrounds the rear end portion 12 of the metallic shell 50 and the separator 200 for their protection. That opening end 46 located at the forward side CL1 of the tubular housing 45 is engaged with the outer circumference of the rear-end engagement portion 57 of the metallic shell 50, is crimped from radially outside, and is full-circle laser-welded to the rear-end engagement portion 57. By this procedure, the tubular housing 45 is attached to the metallic shell 50.

A tubular metal holding member 70 is provided in a gap between the tubular housing 45 and the separator 200. The metal holding member 70 has a support portion 71 formed by bending its rear end inward. The support portion 71 butts against a collar portion 201 provided at a rear-end outer circumference of the separator 200. Thus, the metal holding member 70 supports the separator 200. In a state in which the metal holding member 70 supports the separator 200, the outer circumferential surface of the tubular housing 45 is crimped at a position corresponding to the metal holding member 70, whereby the metal holding member 70 which supports the separator 200 is fixed to the tubular housing 45.

Furthermore, a grommet 75 is provided on the rear side of the separator 200. The grommet 75 closes the tubular housing 45 at its rear end. The grommet 75 has five lead wire insertion holes 76 (FIG. 1 shows one of them) for allowing the five lead wires 78 to extend outward therethrough.

Figure 2:
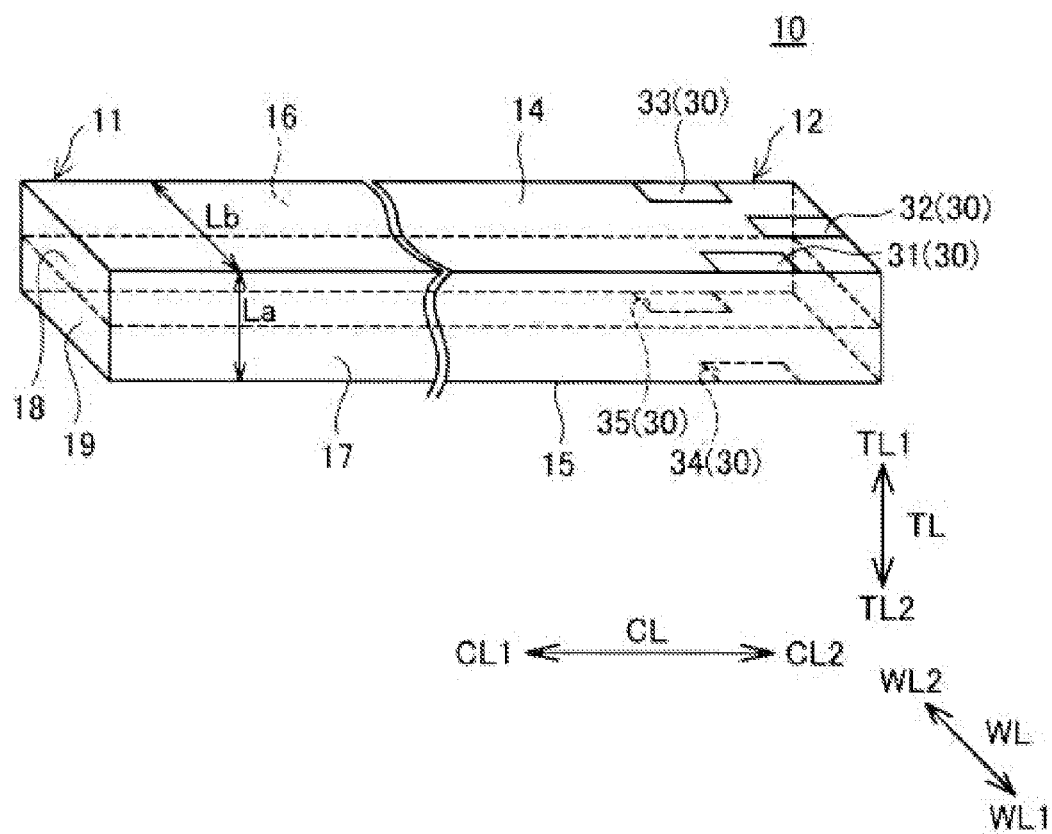
[FIG. 2] View for explaining the constitution of a detection element.

FIG. 2 is a view for explaining the constitution of the detection element 10. FIG. 2 schematically shows the detection element 10. The detection element 10 has a first main surface 14 and a second main surface 15 which constitute a portion of the surface thereof, and a first side surface 16 and a second side surface 17 which constitute another portion of the surface. The first main surface 14 and the second main surface 15 extend along the axial direction CL. The first main surface 14 and the second main surface 15 face opposite each other. The first side surface 16 and the second side surface 17 extend along the axial direction CL. The first side surface 16 and the second side surface 17 face opposite each other. The first main surface 14 and the second main surface 15 are greater in surface area than the first side surface 16 and the second side surface 17.

A direction in which the first main surface 14 and the second main surface 15 face opposite each other is defined as a thickness direction TL of the detection element 10, and a direction in which the first side surface 16 and the second side surface 17 face opposite each other (a direction which is along the first main surface 14 and the second main surface 15 and which is orthogonal to the axial direction CL) is defined as a width direction WL of the detection element 10. The thickness direction TL directed from the second main surface 15 toward the first main surface 14 is defined as a first thickness direction TL1, and the thickness direction TL directed from the first main surface 14 toward the second main surface 15 is defined as a second thickness direction TL2. The width direction WL directed from the first side surface 16 toward the second side surface 17 is defined as a first width direction WL1, and the width direction WL directed from the second side surface 17 toward the first side surface 16 is defined as a second width direction WL2. As shown in FIG. 2, La represents the length of the detection element 10 along the thickness direction TL, and Lb represents the length of the detection element 10 along the width direction WL. The detection element 10 satisfies the relational expression "Lb>La."

The detection element 10 is configured such that an element 18 and a heater 19 are laminated together in the thickness direction TL. The element 18 and the heater 19 each have a plate-like form extending along the axial direction CL. As viewed from the axial direction CL, the detection element 10 has a rectangular shape whose longitudinal direction coincides with the width direction WL and which has four edges substantially perpendicular to each other. The detection element 10 used in a full range air/fuel ratio sensor is publicly known, but its schematic configuration will be described below.

The element 18 is composed of an oxygen concentration cell element configured such that porous electrodes are formed on opposite sides of a solid electrolyte substrate; an oxygen pump element configured such that porous electrodes are formed on opposite sides of a solid electrolyte substrate; and a spacer sandwiched between these two elements to thereby form a hollow measuring gas chamber. The solid electrolyte substrates are formed of zirconia which contains yttria as a stabilizer in solid solution. The porous electrodes are formed primarily of Pt. The spacer used to form the measuring gas chamber is formed primarily of alumina. One porous electrode of the oxygen concentration cell element and one porous electrode of the oxygen pump element are disposed in such a manner as to be exposed to the interior of the hollow measuring gas chamber. The measuring gas chamber is formed in the forward end portion 11 of the detection element 10, and the portion where the measuring gas chamber is formed corresponds to the detection portion. The heater 19 is formed such that a heat-generating resistor pattern formed primarily of Pt is sandwiched between insulating substrates formed primarily of alumina.

Three electrode terminals 31, 32, and 33 are disposed on a portion that is located toward the rear side CL2 of the first main surface 14 of the detection element 10. Two electrode terminals 34 and 35 are disposed on a portion that is located toward the rear side CL2 of the second main surface 15 of the detection element 10. Here, when the electrode terminals 31 to 35 are to be generically referred to, the term "electrode terminals 30" is used.

In the present embodiment, the electrode terminals 31 to 33 are disposed along the width direction WL. That is, the electrode terminals 31 to 33 are disposed at positions shifted from one another in the width direction WL. The electrode terminal 32 is disposed at a position located further toward the rear side CL2 in the axial direction CL than the electrode terminals 31 and 33. The electrode terminals 34 and 35 are disposed along the width direction WL. That is, the electrode terminals 34 and 35 are disposed at positions shifted from each other in the width direction WL. Further, the electrode terminals 34 and 35 are disposed so as to overlap with the electrode terminals 31 and 33 in the axial direction CL, respectively, and are disposed so as to be offset from the electrode terminal 32 in the axial direction CL, respectively. Here, the electrode terminals 31 to 33 correspond to the "first electrode terminal portion" in the appended claims, and the electrode terminals 34 and 35 correspond to the "second electrode terminal portion" in the appended claims. Further, the electrode terminal 32 corresponds to the "specific first electrode terminal portion" in the appended claims, and the electrode terminals 31 and 33 correspond to the "other first electrode terminal portion" in the appended claims.

The first to third electrode terminals 31 to 33 are formed on the element 18, and one of the first to third electrode terminals 31 to 33 is electrically connected, in common, to one porous electrode of the oxygen concentration cell element exposed to the interior of the measuring gas chamber and to one porous electrode of the oxygen pump element. The remaining two of the first to third electrode terminals 31, 32, and 33 are electrically connected to the other porous electrode of the oxygen concentration cell element and to the other porous electrode of the oxygen pump cell, respectively. The fourth and fifth electrode terminals 34 and 35 are formed on the heater 19 and are connected to opposite ends, respectively, of the heat-generating resistor pattern through vias (not shown) extending through the heater 19 in the thickness direction.

A-2. Detailed Constitution of Terminal Members

Figure 3:
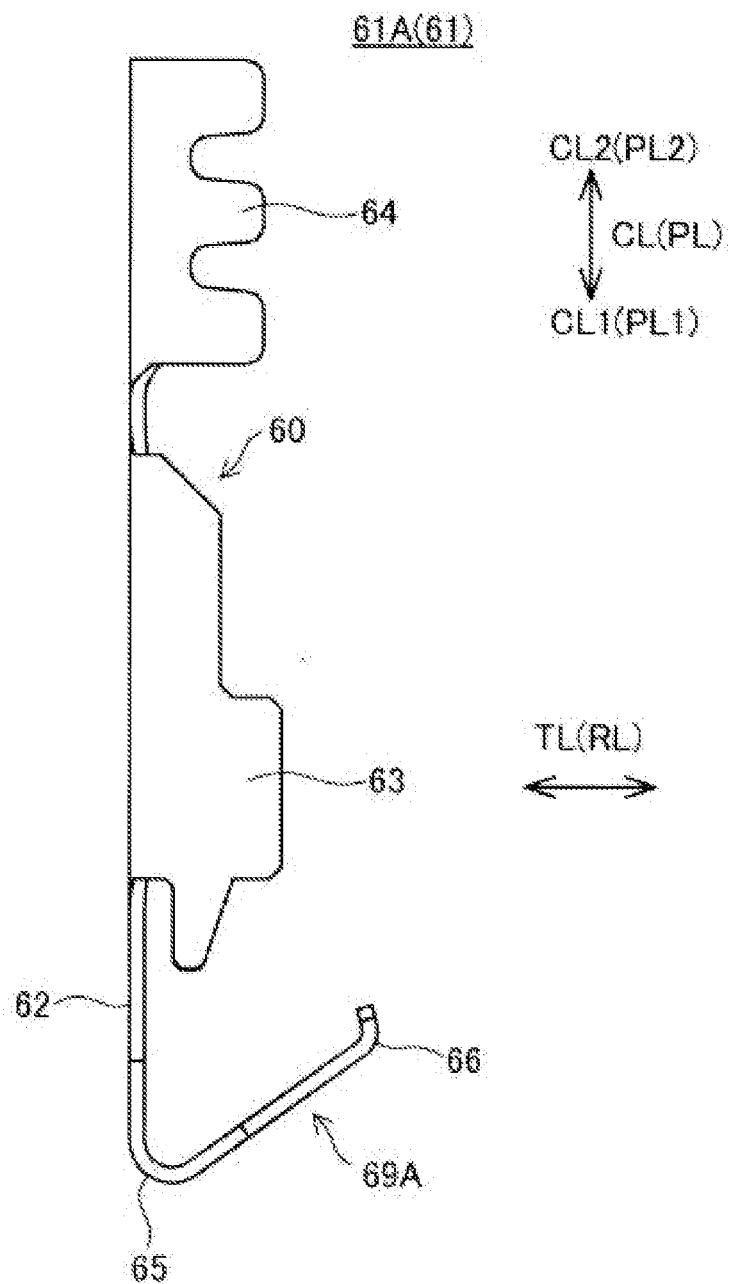
[FIG. 3] Side view of a first-type terminal member.
Figure 4:
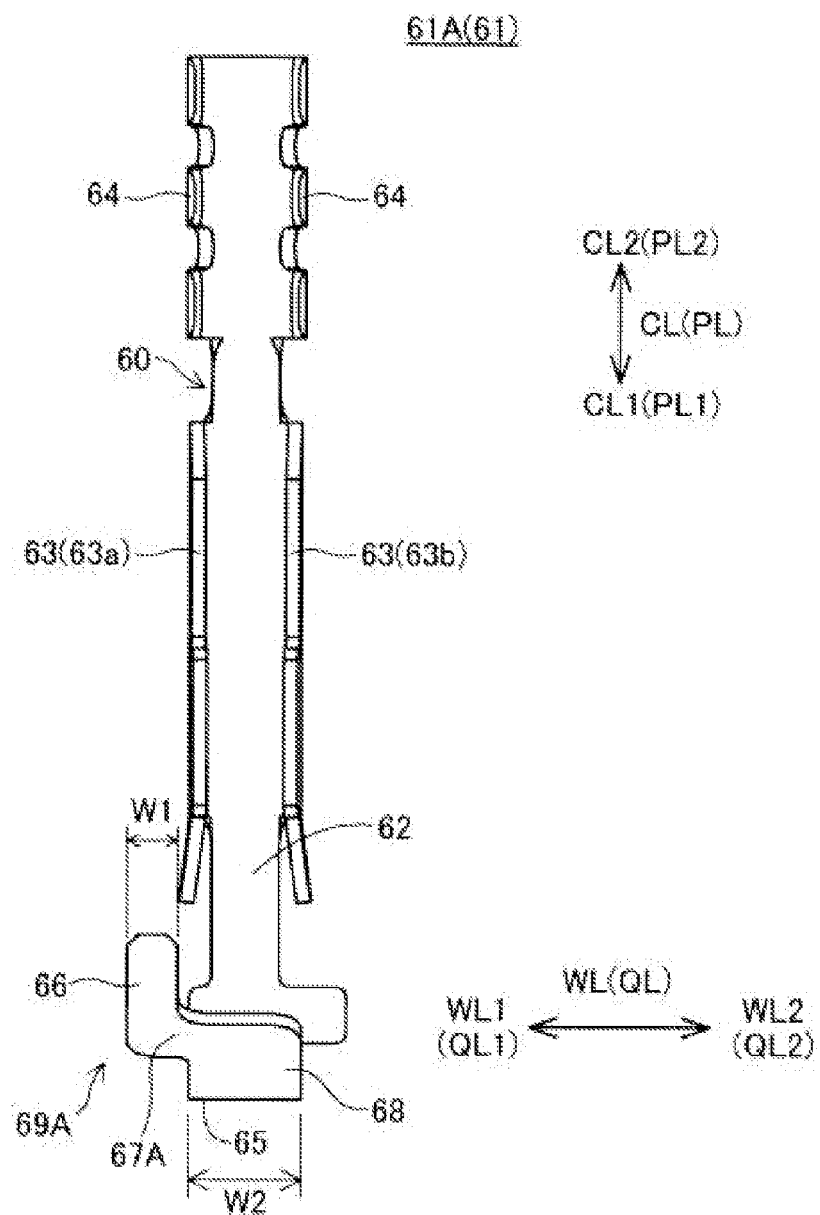
[FIG. 4] Front view of the first-type terminal member.
Figure 5:
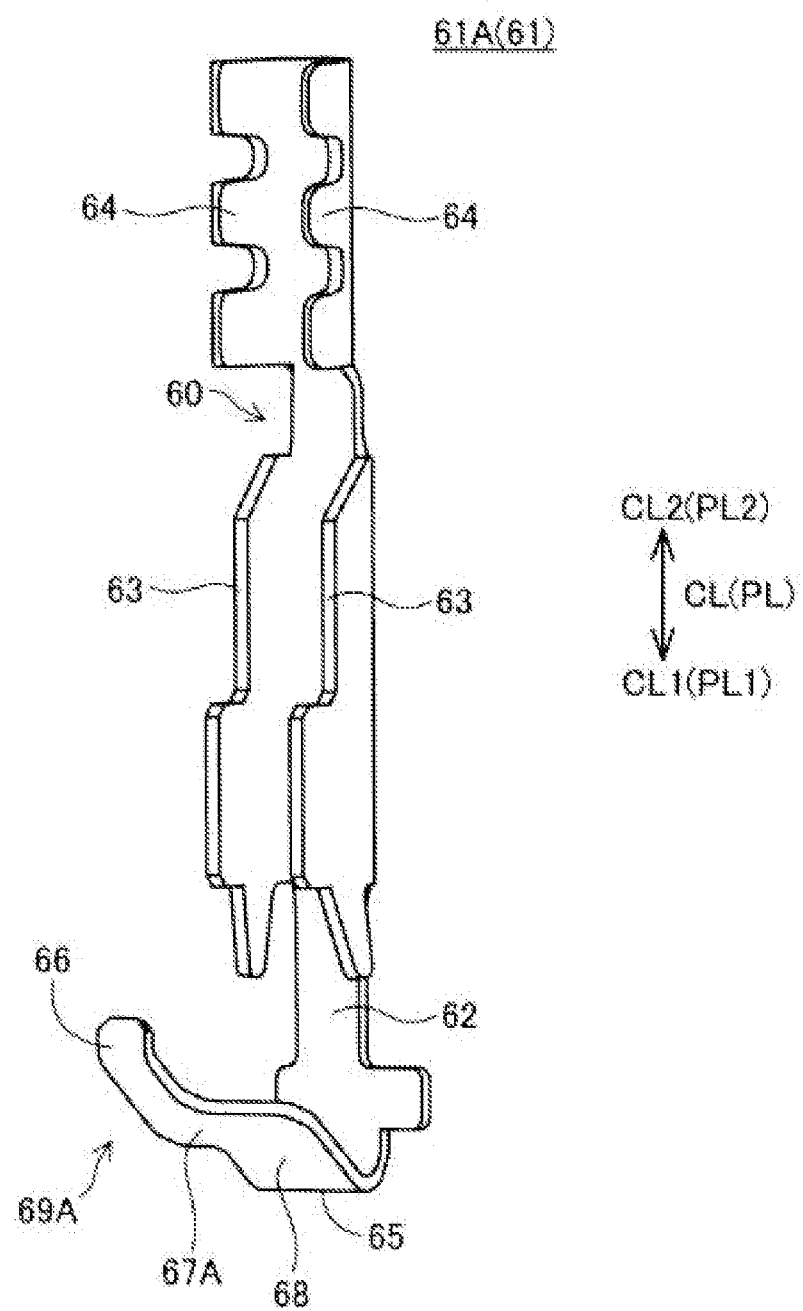
[FIG. 5] Perspective view of the first-type terminal member.
Figure 6:
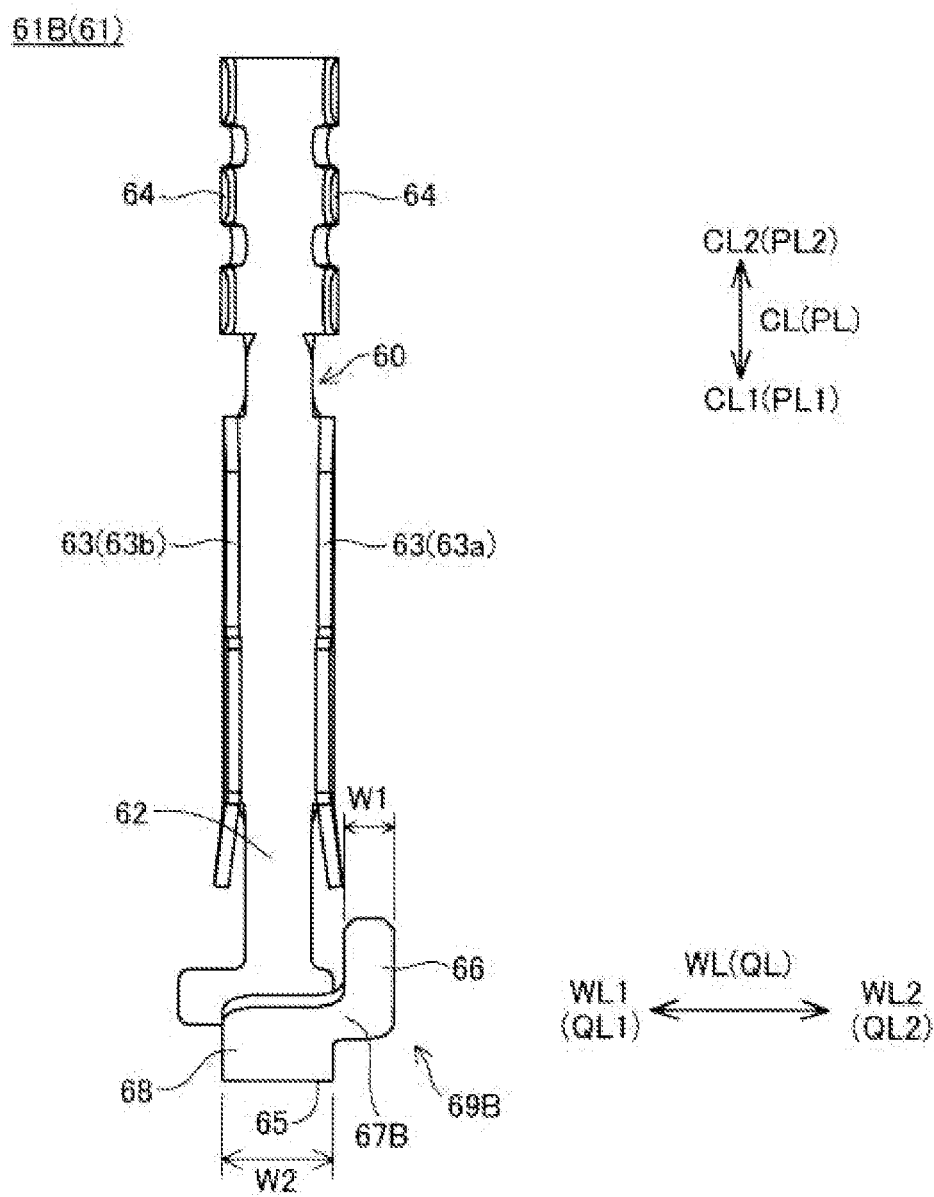
[FIG. 6] Front view of a second-type terminal member.
Figure 7:
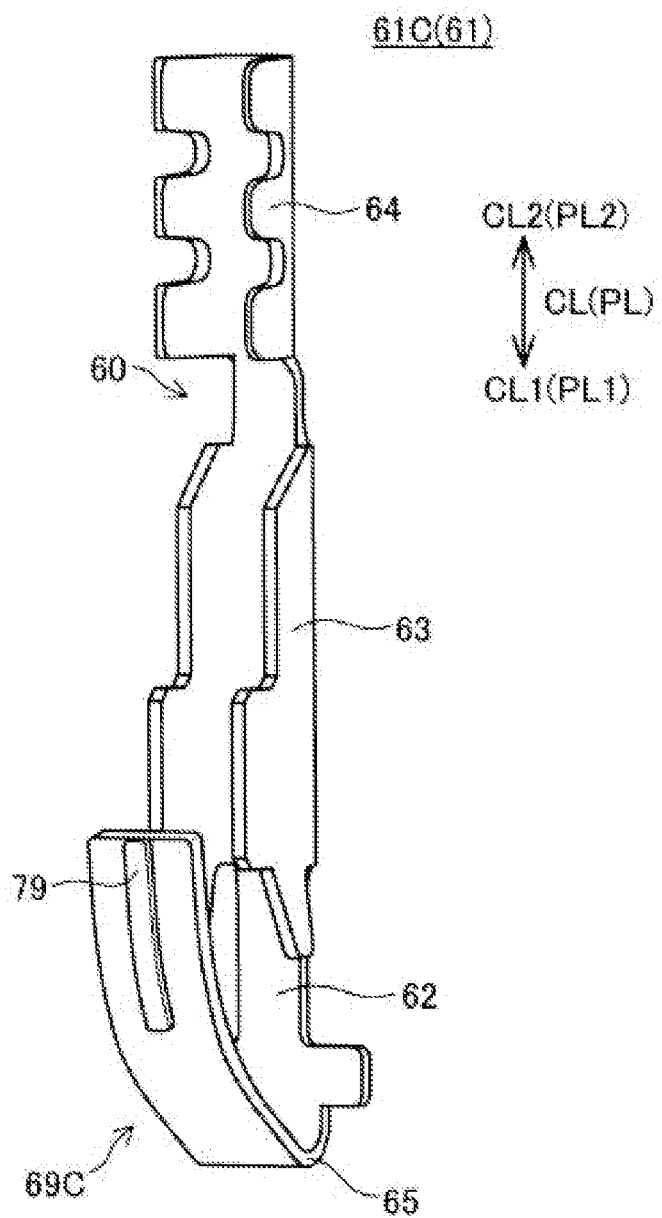
[FIG. 7] Perspective view of a third-type terminal member.

FIG. 3 is a side view of the first-type terminal member 61A. FIG. 4 is a front view of the first-type terminal member 61A. FIG. 5 is a perspective view of the first-type terminal member 61A. FIG. 6 is a front view of the second-type terminal member 61B. FIG. 7 is a perspective view of the third-type terminal member 61C. In the present specification, when the first to third terminal members 61A to 61C are to be generically referred to without being distinguished from one another, the term "terminal members 61" is used.

The first-type terminal member 61A is used with the electrode terminal 33 and the electrode terminal 34; the second-type terminal member 61B is used with the electrode terminal 31 and the electrode terminal 35; and the third-type terminal member 61C is used with the electrode terminal 32.

The terminal members 61 are formed of metal such as INCONEL or stainless steel. Preferably, material used to form the terminal members 61 can maintain spring elasticity even when repeatedly exposed to high temperature.

As shown in FIGS. 3 to 5, the first-type terminal member 61A includes a frame body portion 60, a folded portion 65, and the element contact portion 69A. The frame body portion 60 has an elongated shape extending along the axial direction CL. In the first-type terminal member 61A, a direction in which the frame body portion 60 extends is defined as a longitudinal direction PL. When the terminal member 61A is incorporated into the gas sensor 1, the longitudinal direction PL and the axial direction CL coincide with each other.

As shown in FIGS. 4 and 5, the frame body portion 60 has a body 62, a connection portion 64, and a pair of positioning portions 63. The body 62 is a plate-like member extending along the axial direction CL. The connection portion 64 is formed at the rear side CL2 of the frame body portion 60. In a state in which the corresponding lead wire 78 is inserted into the connection portion 64, the connection portion 64 is crimped inward, thereby holding the lead wire 78. By this procedure, the lead wire 78 and the first-type terminal member 61A are electrically connected to each other. The paired positioning portions 63 are plate-like members protruding from opposite sides, with respect to the width direction WL, of the body 62. By means of the positioning portions 63 being at least partially accommodated in the separator 200, movement of the terminal member 61A in the width direction WL is restricted. The paired positioning portions 63 form the sides, with respect to the width direction WL, of the frame body portion 60. In a state in which the terminal member 61A is incorporated into the gas sensor 1, one of the paired positioning portions 63 which is located inward with respect to the width direction WL of the detection element 10 is referred to as a positioning portion 63a, and the other one located outward with respect to the width direction WL as a positioning portion 63b.

As shown in FIG. 3, the folded portion 65 connects the frame body portion 60 and the element contact portion 69A. The folded portion 65 is folded such that the element contact portion 69A extends toward the rear side CL2. That is, the folded portion 65 is a portion that is located furthest toward the forward side CL1 of the terminal member 61A.

As shown in FIG. 3, the element contact portion 69A faces the frame body portion 60. As shown in FIGS. 4 and 5, the element contact portion 69A has a base portion 68, a contact portion 66, and a turning portion 67A. The base portion 68 is connected to the folded portion 65. The contact portion 66 actually comes into contact with the electrode terminal 30. The turning portion 67A is located between the contact portion 66 and the folded portion 65 and between the contact portion 66 and the base portion 68. A side of the element contact portion 69A toward the folded portion 65 is referred to as a contact-portion forward side PL1, and a side toward the turning portion 67A as a contact-portion rear side PL2. In the terminal member 61A, a direction which is orthogonal to the axial direction CL and in which the frame body portion 60 and the element contact portion 69A face each other is referred to as a thickness direction RL of the terminal member 61A. When the terminal member 61A is incorporated into the gas sensor 1, the thickness direction RL of the terminal member 61A and the thickness direction TL of the detection element 10 coincide with each other. A direction orthogonal to the axial direction CL and to the thickness direction RL is referred to as a width direction QL of the terminal member 61A. When the terminal member 61A is incorporated into the gas sensor 1, the width direction QL and the width direction WL coincide with each other. The width direction QL of the terminal member 61A which corresponds to the first width direction WL1 of the detection element 10 is referred to as a first width direction QL1, and a direction corresponding to the second width direction WL2 of the detection element 10 as a second width direction QL2.

The contact portion 66 moves through elastic deformation with the folded portion 65 serving as a fulcrum. A width W1 of the contact portion 66 is narrower than a width W2 of the folded portion 65. The contact portion 66 may assume the form of a protrusion provided on that surface of the element contact portion 69A which faces the detection element 10. An example of the protrusion is a protrusion 79 of the third-type terminal member 61C (FIG. 7), which will be described later. In this case, the width W1 of the contact portion 66 means the width of the protrusion.

As shown in FIG. 4, the turning portion 67A turns toward the width direction WL. More specifically, the turning portion 67A turns toward the first width direction WL1 from the base portion 68 to the contact portion 66. Thus, the contact portion 66 is disposed at a position shifted in the width direction WL from the folded portion 65. The terminal member 61A is incorporated into the gas sensor 1 such that the turning portion 67A turns inward with respect to the width direction WL. That is, the turning portion 67A is located inward with respect to the width direction WL of the detection element 10 in the course from the base portion 68 to the contact portion 66.

As shown in FIG. 6, the second-type terminal member 61B assumes the form of a mirror image of the first-type terminal member 61A shown in FIG. 4. That is, a turning portion 67B of an element contact portion 69B turns toward an opposite direction of the first-type terminal member 61A. Other constitutional features are similar to those of the first-type terminal member 61A. Thus, the similar constitutional features are denoted by the same reference numerals as those of the first-type terminal member 61A, and repeated description thereof is omitted. The turning portion 67B turns toward the second width direction WL2 in the course from the base portion 68 to the contact portion 66.

As shown in FIG. 7, the third-type terminal member 61C differs from the first-type terminal member 61A in the constitution of an element contact portion 69C. Other constitutional features are similar to those of the first-type terminal member 61A; thus, the similar constitutional features are denoted by the same reference numerals as those of the first-type terminal member 61A, and repeated description thereof is omitted. The element contact portion 69C does not have the turning portion 67A (68B). Also, the element contact portion 69C has the protrusion 79. The protrusion 79 actually comes into contact with the second electrode terminal 32.

A-3. Detailed Constitution of Separator 200

Figure 8:
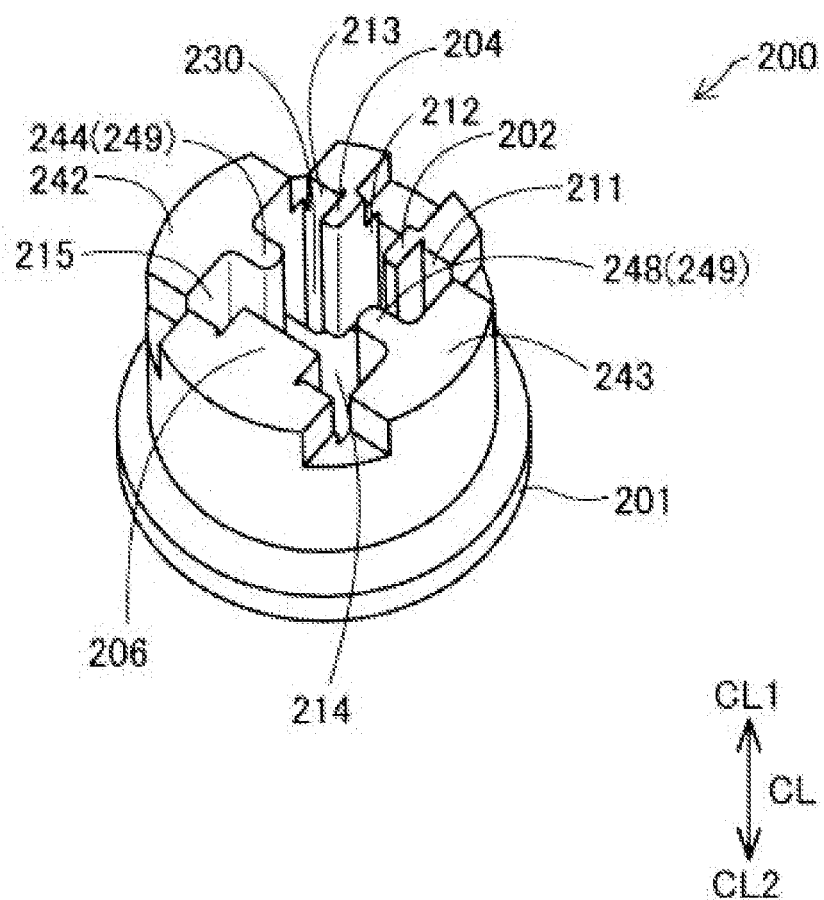
[FIG. 8] Perspective view of a separator.
Figure 9:
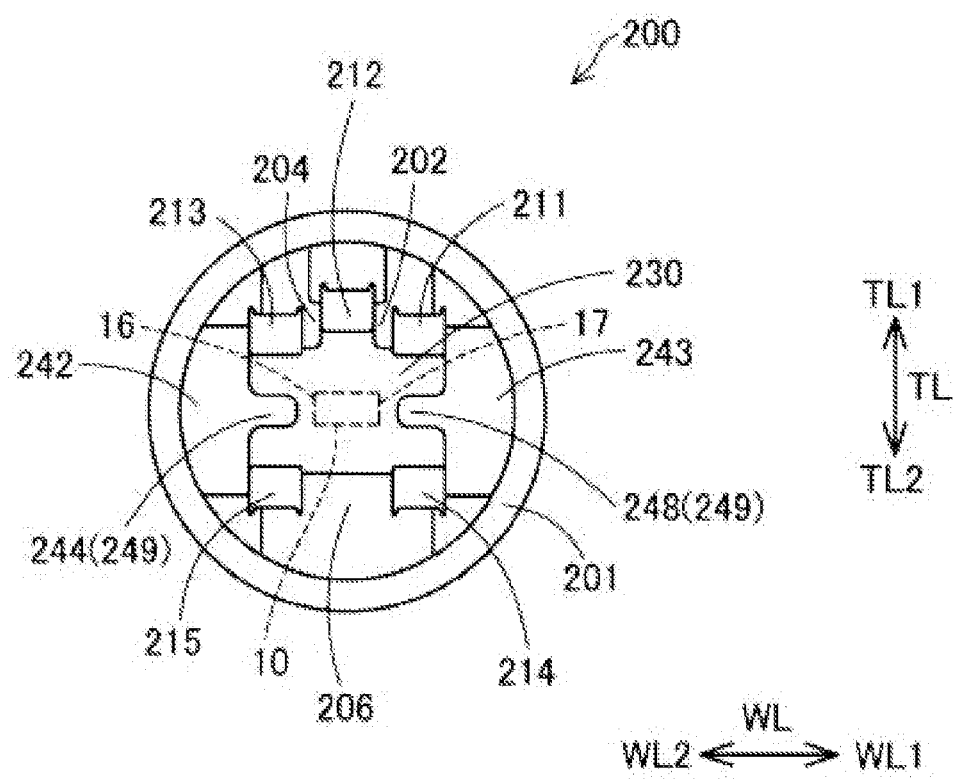
[FIG. 9] View of the separator as viewed from the forward side with respect to an axial direction CL.

FIG. 8 is a perspective view of the separator 200. FIG. 9 is a view of the separator 200 as viewed from the forward side CL1 with respect to the axial direction CL. For easy understanding, in FIG. 9, the detection element 10 is represented by the dotted line. As shown in FIGS. 8 and 9, the separator 200 has an accommodation chamber 230 which is a through hole extending therethrough in the axial direction CL from its forward end to its substantial center.

The accommodation chamber 230 has, at an outer circumferential portion of the separator 200, first to fifth terminal accommodation chambers 211 to 215 which are through holes extending in the axial direction CL through the separator 200 from the forward end to the rear end of the separator 200. The separator 200 has three partition walls 202, 204, and 206 and two side partition walls 244 and 248 in the accommodation chamber 230. The first terminal accommodation chamber 211 and the fifth terminal accommodation chamber 215 each accommodate the second-type terminal members 61B. The third terminal accommodation chamber 213 and the fourth terminal accommodation chamber 214 each accommodate the first-type terminal member 61A. The second terminal accommodation chamber 212 accommodates the third-type terminal member 61C. The first to fifth terminal chambers 211 to 215 each accommodate a portion that is located toward the forward side CL1 of the frame body portion 60.

The first partition wall 202 is disposed between the first terminal accommodation chamber 211 and the second terminal accommodation chamber 212. The second partition wall 204 is disposed between the second terminal accommodation chamber 212 and the third terminal accommodation chamber 213. The third partition wall 206 is disposed between the fourth terminal accommodation chamber 214 and the fifth terminal accommodation chamber 215. The first to third partition walls 202, 204, and 206 are members of the separator 200 and are formed of electrically insulating ceramic. The first to third partition walls 202, 204, and 206 extend along the axial direction CL in the accommodation chamber 230.

As shown in FIG. 9, the first side partition wall 244 faces the first side surface 16 of the detection element 10. The first side partition wall 244 protrudes toward the first side surface 16 of the detection element 10 from a peripheral wall 242 which partially constitutes the outer circumference of the separator 200. The first side partition wall 244 is located between the third terminal accommodation chamber 213 and the fifth terminal accommodation chamber 215. That is, the first side partition wall 244 is located between the paired terminal members 61A and 61B which are disposed in a facing manner on opposite sides of the detection element 10 with respect to the thickness direction TL.

As shown in FIG. 9, the second side partition wall 248 faces the second side surface 17 of the detection element 10. The second side partition wall 248 protrudes toward the second side surface 17 of the detection element 10 from a peripheral wall 243 which partially constitutes the outer circumference of the separator 200. The second side partition wall 248 is located between the first terminal accommodation chamber 211 and the fourth terminal accommodation chamber 214. That is, the second side partition wall 248 is located between the paired terminal members 61A and 61B which are disposed in a facing manner on opposite sides of the detection element 10 with respect to the thickness direction TL. The first and second side partition walls 244 and 248 are members of the separator 200 and are formed of electrically insulating ceramic. The first and second side partition walls 244 and 248 extend along the axial direction CL in the accommodation chamber 230. When the first and second side partition walls 244 and 248 are to be generically referred to without being distinguished from each other, the term "side partition walls 249" is used.

Figure 10:
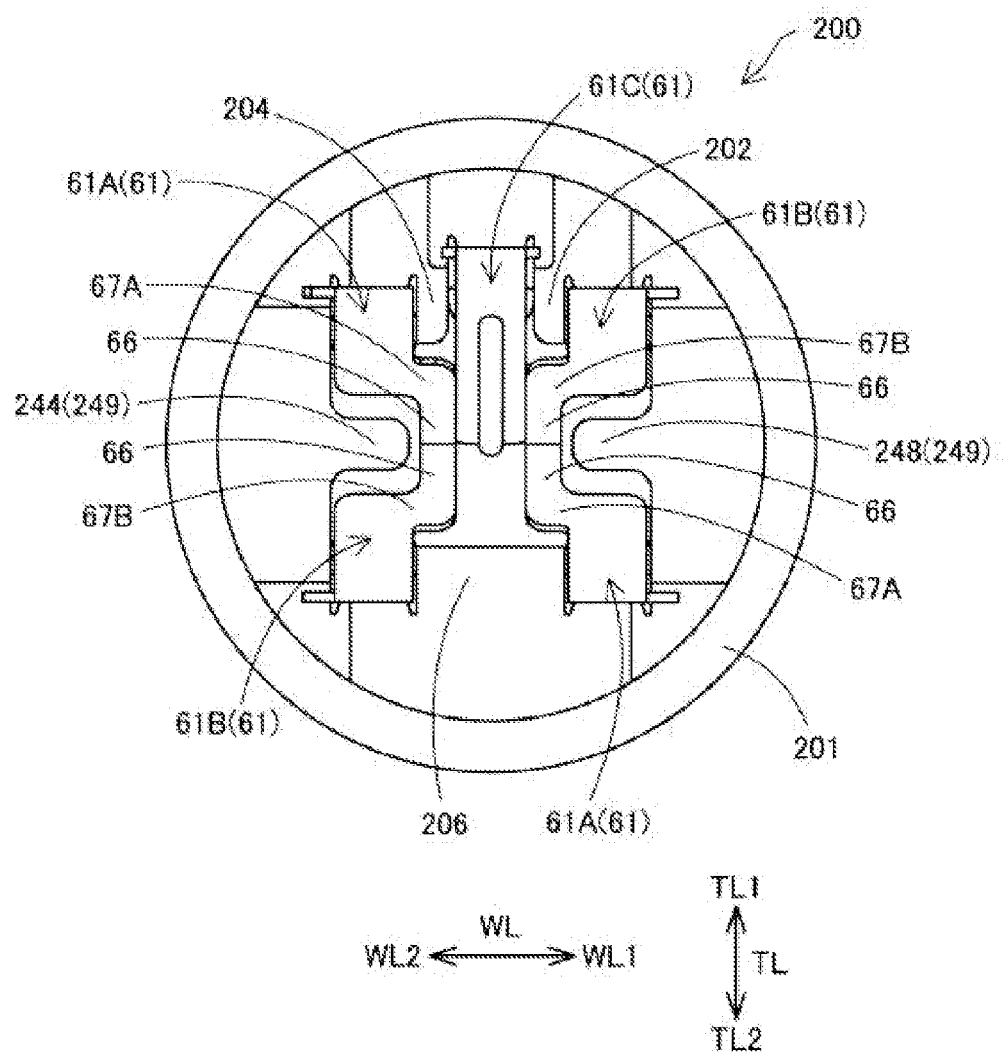
[FIG. 10] View showing the separator in which the terminal members are accommodated.
Figure 11:
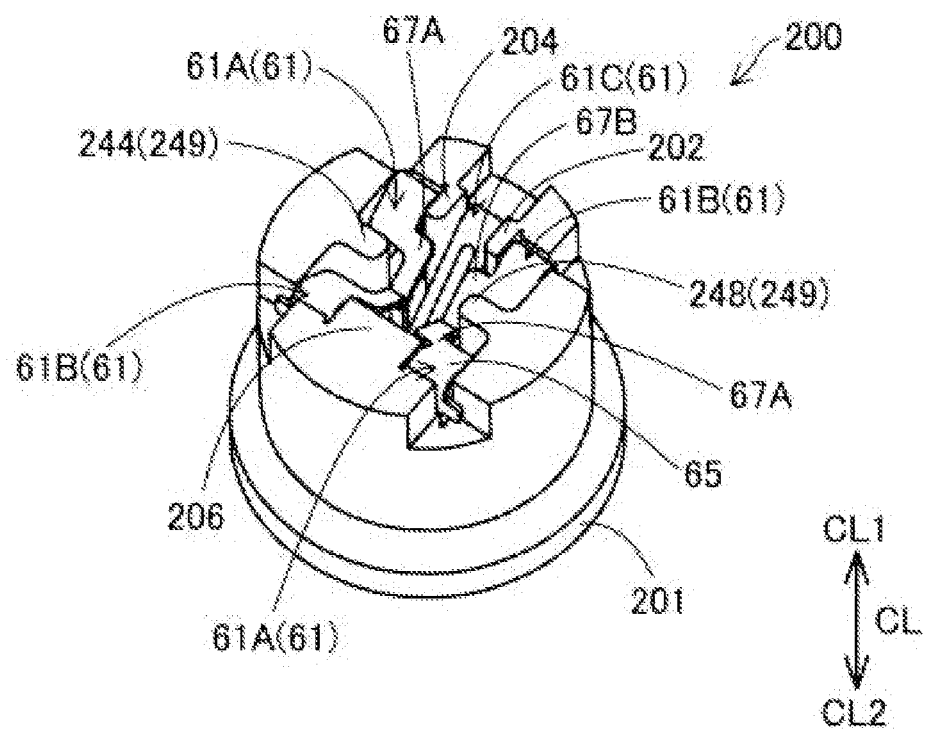
[FIG. 11] Perspective view of the separator of FIG. 10.

FIG. 10 shows the separator 200 in which the terminal members 61 are accommodated. FIG. 10 is a view of the separator 200 as viewed from the forward side CL1 with respect to the axial direction CL. When the detection element 10 and the terminal members 61 are to be incorporated into the separator 200, first, as shown in FIGS. 10 and 11, the terminal members 61 are disposed in the separator 200.

Figure 12:
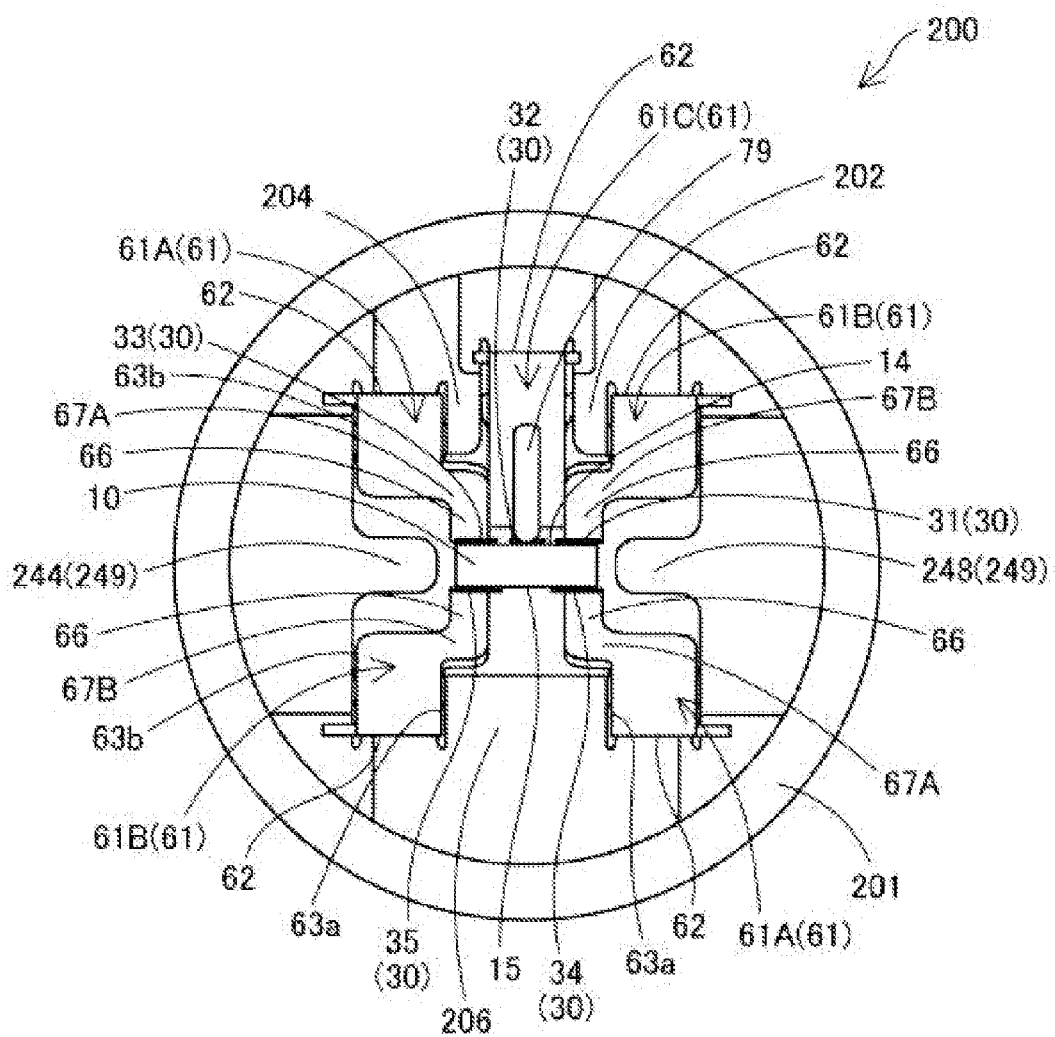
[FIG. 12] view of the separator in which the terminal members and the detection element are accommodated, as viewed from the forward side with respect to the axial direction CL.
Figure 12:
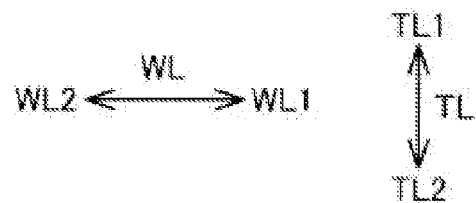

FIG. 12 is a view of the separator 200 in which the terminal members 61 and the detection element 10 are accommodated, as viewed from the forward side CL1 with respect to the axial direction CL. After the terminal members 61 are accommodated into the separator 200, the rear end portion 12 of the detection element 10 is inserted into the separator 200 toward the rear side CL2 with respect to the axial direction CL such that the electrode terminals 30 come into contact with the connection portions 66 and 79, respectively. As a result of insertion of the rear end portion 12 of the detection element 10 into the separator 200, the element contact portions 69A, 69B, and 69C (FIGS. 5 to 7) move toward the frame body portions 60 (FIGS. 5 to 7), respectively. Thus, the contact portions 66 and 79 come into elastic contact with the electrode terminals 30, respectively.

A-4. Inventive Aspect of the First Embodiment:

In the first embodiment, as shown in FIG. 2, the three electrode portions 31 to 33 are formed on the first main surface 14, while the two electrode terminal portions 34, 35 are formed on the second main surface 15 of the detection element 10. The electrode terminal portion 32 on the first main surface 14 is positioned so as to be offset from the other two electrode terminal portions 31, 33 in the axial direction CL of the detection element 10. In addition, the other two electrode terminal portions 31, 33 on the first main surface 14 are positioned so as to overlap with the two electrode terminal portions 34, 35 on the second main surface in the axial direction CL of the detection element 10.

As shown in FIG. 12, in the thickness direction TL of the detection element 10, a distance between the detection element 10 and the frame body portion 60 (in particular, the body 62 in FIG. 7) of the terminal member 61C, which is brought into contact with the electrode terminal portion 32, is larger than distances between the detection element 10 and the frame body portions 60 (in particular, the bodies 62 in FIGS. 5, 6) of the terminal members 61A, 61B, which are brought into contact with the electrode terminal portions 31, 33, respectively,. Namely, in FIG. 12, the body 62 of the terminal member 61C is disposed so as to be positioned further upwards in the drawing than the bodies 62 of the two terminal members 61A, 61B which lie on both the sides thereof. Consequently, the distance from the frame body portion 60 to the contact portion (the protrusion 79 in FIG. 7) of the terminal member 61C is larger than the distances from the frame body portions 60 to the contact portions 66 (FIGS. 5, 6) of the other terminal members 61A, 61B. Additionally, the three types of terminal members 61A to 61C are formed of the same metallic members. Consequently, the spring force of the terminal member 61C becomes weaker than the spring forces of the other two terminal members 61A, 61B. Here, with respect to the thickness direction TL of the detection element 10, each distance between the frame body portion 60 (in particular, the body 62 in FIG. 7) of the terminal member 61C and the frame body portions 60 (in particular, the bodies 62 in FIGS. 5, 6) of the terminal members 61A, 61B is 1 mm. Further, with respect to the axial direction CL of the detection element 10, each distance between a contact portion between the electrode terminal portion 32 and the frame body portion 60 of the terminal member 61C and each contact portion between the electrode terminal portions 31, 33 and the frame body portions 60 of the terminal members 61A, 61B is 1 mm.

As was described in the prior art technique, adopting the arrangement in which the electrode terminal portion 32 is offset in the axial direction CL as shown in FIG. 2 causes the imbalance in the force exerted from the whole of the terminal members 61A to 61C to the detection element 10. When this imbalance in the force becomes too large, there is caused a possibility that a sufficient electrical connection cannot be ensured between a part of the plurality of electrode terminal portions 31 to 33 and a part of the plurality of terminal members 61A to 61C. In addition, when the detection element 10 is inserted into the separator 200 (10) to which the terminal members 61A to 61C are assembled from the rear end side thereof, in the event that the imbalanced force is exerted on the detection terminal 10, the detection element 10 is inclined minutely, resulting in a situation in which the smooth insertion of the detection element 10 is impaired. In contrast with this, in this embodiment, the frame body portion 60 of the terminal member 61C which is positioned so as to be offset in the axial direction CL is disposed so as to be positioned farther away from the detection element 10 than the frame body portions 60 of the other terminal members 61A, 61B. Therefore, the element contact portion 69C of the terminal member 61C becomes longer accordingly, whereby the spring force thereof becomes weaker. Namely, the force exerted on the electrode terminal portion 32 from the terminal member 61C becomes weaker than the forces exerted on the electrode terminal portions 31, 33 from the other terminal members 61A, 61B. That is, in the electrode terminal portions 31 to 33 which are provided on the first main surface 14, even though the electrode terminal portion 32 is disposed so as to be offset from the other electrode terminal portions 31, 33 in the axial direction CL and the electrode terminal portion 32 is disposed so as to be offset from the electrode terminal portions 34, 35 provided on the second main surface 15 in the axial direction, the force exerted on the electrode terminal portion 32 from the terminal member 61C is reduced, whereby the forces exerted to the electrode terminal portions 31, 33 from the terminal members 61A, 61B and the forces exerted on the electrode terminal portions 34, 35 from the terminal members 61A, 61B affect the force exerted to the detection element 10 from the whole of the terminal members 61. As a result, it is possible to mitigate the influence imposed by the problem that the balance of the forces exerted on the two main surfaces 14, 15 of the detection element 10 is impaired excessively to thereby make incomplete the electrical connection between a part of the electrode terminal portions and a part of the terminal members.

In addition, in this embodiment, the two electrode terminal portions 34, 35 on the second main surface 15 and the two electrode terminal portions 31, 33 on the first main surface 14 are disposed in the same position in the axial direction CL of the detection element 10. Additionally, with respect to the thickness direction of the detection element 10, a distance between the detection element 10 and the frame body portions 60 of the terminal members 61A, 61B, which are brought into contact with the two electrode terminal portions 34, 35 on the second main surface 15, is the same as the distance between the detection element 10 and the frame body portions 60 of the terminal members 61A, 61B, which are brought into contact with the two electrode terminal portions 31, 33 on the first main surface 14. In the event that this configuration is adopted, the forces exerted individually on the electrode terminal portions 31, 33 from the terminal members 61A, 61B which are brought into contact with the electrode terminal portions 31, 33 and the forces exerted individually on the electrode terminal portions 34, 35 from the terminal members 61A, 61B which are brought into contact with the electrode terminal portions 34, 35 can be made almost the same, whereby the force exerted on the detection element 10 from the whole of the terminal members 61 tends to be well balanced easily. As a result, it is possible to mitigate further the influence imposed by the problem that the balance of the forces exerted on the two main surfaces 14, 15 of the detection element 10 is impaired excessively to thereby make incomplete the electrical connection between part of the electrode terminal portions and part of the terminal members. In this respect, it is preferable to configure these terminal members so that the forces exerted individually on the electrode terminal portions 31, 33 on the first main surface 14 from the terminal members 61A, 61B which are brought into contact with the electrode terminal portions 31, 33 and the forces exerted individually on the electrode terminal portions 34, 35 on the second main surface 15 from the terminal members 61A, 61B which are brought into contact with the electrode terminal portions 34, 35 become the same. It is noted that, in this specification, the phrase that the plurality of forces become the "same" means that the forces are in the range of ±10% of an average value of the forces.

Further, in this embodiment, the electrode terminal portions 31, 33 and the electrode terminal portions 34, 35 are disposed so as to overlap with each other in the width direction WL. In the event that this configuration is adopted, the forces exerted individually on the electrode terminal portions 31, 33 from the terminal members 61A, 61B which are brought into contact with the electrode terminal portions 31, 33 and the forces exerted individually on the electrode terminal portions 34, 35 from the terminal members 61A, 61B which are brought into contact with the electrode terminal portions 34, 35 are symmetrical with each other across the detection element 10 also in the width direction, whereby the force exerted on the detection element 10 from the whole of the terminal members 61 tends to be better balanced easily. As a result, it is possible to mitigate further the influence imposed by the problem that the balance of the forces exerted on the two main surfaces 14, 15 of the detection element 10 is impaired excessively to thereby make incomplete the electrical connection between part of the electrode terminal portions and part of the terminal members.

In this embodiment, although the three electrode terminal portions 31 to 33 are provided on the first main surface 14 and the two electrode terminal portions 34, 35 are provided on the second main surface 15, the numbers of electrode terminal portions and the terminal members and the arrangement thereof can be altered arbitrarily as required. However, it is preferable that three or more electrode terminal portions are provided on the first main surface 14 and that two or more electrode terminal portions are provided on the second main surface 15. In this event, it is preferable that in the three or more electrode terminal portions 31 to 33 on the first main surface 14, at least one specific electrode terminal portion is disposed so as to be offset from the other electrode terminal portions than the specific electrode terminal portion in the axial direction CL of the detection element 10.

In this embodiment, with respect to the thickness direction TL of the detection element 10, each distance between the frame body portion 60 (in particular, the body 62 in FIG. 7) of the terminal member 61C and the frame body portions 60 (in particular, the bodies 62 in FIGS. 5, 6) of the terminal members 61A, 61B is 1 mm. However, this distance is not limited thereto. However, it is preferable that this distance is from 0.2 mm to 5 mm.

In the embodiment, with respect to the axial direction CL of the detection element 10, each distance between the contact portion between the electrode terminal portion 32 and the frame body portion 60 of the terminal member 61C and each contact portion between the electrode terminal portions 31, 33 and the frame body portions 60 of the terminal members 61A, 61B is 1 mm. However, this distance is not limited thereto. However, it is preferable that this distance is from 0.2 mm to 10 mm.

In this embodiment, the frame body portion 60 of the terminal member 61C which is brought into contact with the electrode terminal portion 32 corresponds to a "specific first frame body portion" in appended claims, the frame body portions 60 of the terminal members 61A, 61B which are brought into contact with the electrode terminal portions 31, 33 correspond to the "other first frame body portions" of the appended claims, and the frame body portions 60 of the terminal members 61A, 61B which are brought into contact with the electrode terminal portions 34, 35 correspond to "second frame body portions" of the appended claims.

In this embodiment, the distance between the detection element 10 and the frame body portion 60 of the terminal member 61C, which is positioned to be offset in the axial direction CL, is larger than each distance between the detection element 10 and the frame body portions 60 of the other terminal members 61A, 61B. Therefore, the force exerted on the electrode terminal portion 32 from the terminal member 61C becomes weaker than the forces exerted on the electrode terminal portions 31, 33 from the other terminal members 61A, 61B. As a result, it is possible to mitigate further the influence imposed by the problem that the balance of the forces exerted on the two main surfaces 14, 15 of the detection element 10 is impaired excessively to thereby make incomplete the electrical connection between part of the electrode terminal portions and part of the terminal members.

B. Modifications

B-1. First Modification

In the embodiment described above, while the terminal members 61A, 61B have the turning portions 67A, 67B, respectively, a configuration in which the terminal members 61A, 61B do not have the turning portion 67A and the turning portion 67B, respectively, can also be adopted.

B-2. Second Modification

In the embodiment described above, while the detection element 10 includes the five electrode terminal portions 31 to 35, the number of electrode terminal portions is not limited thereto. For example, in the detection element 10, four or more electrode terminal portions may be provided on the first main surface 14, and three or more electrode terminal portions may be provided on the second main surface 15. However, it is preferable that a plurality of electrode terminal portions are disposed on the first main surface 14 and a plurality of electrode terminal portions are also provided on the second main surface 15. Additionally, a configuration may be adopted in which the number of electrode terminal portions formed on the first main surface 14 should be larger by one or more than the number of electrode terminal portions formed on the second main surface 15. According to this configuration, even with a sensor in which the number of electrode terminal portions on a first main surface 14 and the number of electrode terminal portions on a second main surface 15 differ, it is possible to mitigate further the influence imposed by the problem that the balance of the forces exerted on the two main surfaces of the detection element 10 is impaired excessively to thereby make incomplete the electrical connection between part of the electrode terminal portions and part of the terminal members.

B-3. Third Modification

In the embodiment described above, in the five electrode terminal portions 31 to 35 on the detection element 10, the number (two) of electrode terminal portions 31, 33 disposed on the first main surface 14 so as to overlap with each other with respect to their positions along the axial direction CL is the same as the number (two) of electrode terminal portions 34, 35 disposed on the second main surface 15. However, the invention is not limited thereto, and hence, the numbers may differ from each other. In addition, with respect to the axial direction CL, these electrode terminal portions may be disposed in the same positions or may be disposed so that at least a portion of the electrode terminal portions overlap with each other. When used in this specification, the description that the plurality of electrode terminal portions are "disposed so as to be overlap with each other in the axial direction" means both that the electrode terminal portions are disposed in the same positions in the axial direction CL and that only a portion of the electrode terminal portions are disposed so as to overlap with each other in the axial direction CL. In the case of the latter meaning, the forces exerted to the detection element from the whole of the terminal members can be balanced by controlling individually the spring properties of the terminal members which are brought into contact with the terminal electrode portions. Additionally, when used in this specification, the expression that the plurality of electrode terminal portions are "disposed so as to be offset from each other along the axial direction" means both that the electrode terminal portions are disposed so as not to overlap with each other at all in the axial direction CL and only a portion of the electrode terminal portions are disposed so as to overlap with each other with in the axial direction CL.

B-4. Fourth Modification

In the embodiment described above, in the five electrode terminal portions 31 to 35 on the detection element 10, the electrode terminal portions 31, 33 disposed on the first main surface 14 so as to overlap with each other in the axial direction CL and the electrode terminal portions 34, 35 disposed on the second main surface 15 are disposed in the same positions with respect the width direction WL of the detection element 10. However, the electrode terminal portions may be disposed in different positions. However, it is preferable that these electrode terminal portions are disposed so that at least some of the electrode terminal portions overlap with each other in the width direction WL. In this embodiment, the description that the plurality of electrode terminal portions "overlap with each other in the width direction WL" means both that the electrode terminal portions are disposed in the same positions in the width direction WL and that only a portion of the electrode terminal portions are disposed so as to overlap with each other in the width direction WL.

The present invention is not limited to the above-mentioned embodiment and modifications, but may be embodied in various other forms without departing from the spirit of the invention. For example, in order to solve, partially or entirely, the above-mentioned problems or yield, partially or entirely, the above-mentioned effects, technical features of the modes described in the section "Summary of the Invention" and technical features of the modifications can be replaced or combined as appropriate. Also, the technical feature(s) may be eliminated as appropriate unless the present specification mentions that the technical feature(s) is mandatory.

DESCRIPTION OF REFERENCE NUMERALS

1: gas sensor
8: protector
9: detection portion protection layer
10: detection element
11: forward end portion
12: rear end portion
14: first main surface
15: second main surface
16: first side surface
17: second side surface
18: element
20: cup
21: ceramic ring
22: talc ring
23: forward-end peripheral portion
25: opening
26: talc ring
27: sleeve
28: shoulder portion
29: packing
30: electrode terminal
45: tubular housing
46: opening end
50: metallic shell
51: externally threaded portion
52: tool engagement portion
53: crimped portion
54: stepped portion
55: gasket
56: forward-end engagement portion
57: rear-end engagement portion
60: frame body portion
61: terminal member
61A: first-type terminal member
61B: second-type terminal member
61C: third-type terminal member
62: body
63: positioning portion
63*a*: positioning portion (inner side surface)
63*b*: positioning portion (outer side surface)
64: connection portion
65: folded portion
66: contact portion
67A, 67B: turning portion
68: base portion
69, 69A to 69C: element contact portion
70: metal holding member 71: support portion
75: grommet
76: lead wire insertion hole
78: lead wire
79: protrusion
80: outer protector
85: outer introduction hole
90: inner protector
95: inner introduction hole
96: drain hole
97: discharge hole
200: separator
201: collar portion
202: first partition wall
204: second partition wall
206: third partition wall
211: first terminal accommodation chamber
212: second terminal accommodation chamber
213: third terminal accommodation chamber
214: fourth terminal accommodation chamber
215: fifth terminal accommodation chamber
230: accommodation chamber
242: peripheral wall
243: peripheral wall
  0244: first side partition wall
248: second side partition wall
CL1: forward side
W1: width
L1: distance
W2: width
L2: distance
L4: distance
PL: longitudinal direction
QL: width direction
TL: thickness direction
WL: width direction
CL: axial direction
PL1: contact-portion forward side
QL1: first width direction
TL1: first thickness direction
WL1: first width direction
WL2: second width direction
TL2: second thickness direction
CL2: rear side
PL2: contact-portion rear side
QL2: second width direction

The invention claimed is:

1. A sensor comprising:
a detection element extending along an axial direction, and having a first main surface and a second main surface which face opposite each other and constitute a portion of a surface extending along the axial direction, and a plurality of electrode terminal portions disposed on each of the first main surface and the second main surface;
a plurality of terminal members provided in correspondence with the electrode terminal portions and electrically connected to the corresponding electrode terminal portions, each of the terminal members comprising an elongated frame body portion extending along the axial direction, a folded portion connecting with a forward end side of the frame body portion and folded back towards a detection element side and a rearward end side, and an element contact portion connecting with the folded portion at a forward end side thereof and brought into elastic contact with the electrode terminal portion; and
a separator surrounding the element contact portions and a portion of the detection element at which the plurality of electrode terminal portions are disposed,
wherein, with a direction in which the first main surface and the second main surface face opposite each other being defined as a thickness direction,
a plurality of first electrode terminal portions are formed on the first main surface of the detection element, the plurality of first electrode terminal portions including at least one specific first electrode terminal portion and an other first electrode terminal portion other than the specific first electrode terminal portion, and the specific first electrode terminal portion and the other first electrode terminal portion being disposed so as be offset from each other in the axial direction of the detection element,
a plurality of second electrode terminal portions are formed on the second main surface of the detection element,
the second electrode terminal portion is disposed so as to overlap with the other first electrode terminal portion in the axial direction of the detection element and is disposed so as to be offset from the specific first electrode terminal portion in the axial direction of the detection element, and
in the frame body portions of the terminal members, with respect to the thickness direction of the detection element, a distance between the detection element and a specific first frame body portion, which is brought into electrical connection with the specific first electrode terminal portion on the first main surface, is larger than a distance between the detection element and the other first frame body portion, which is brought into electrical connection with the other first electrode portion.

2. The sensor according to claim 1,
wherein, in the frame body portions of the terminal members, with respect to the thickness direction of the detection element, a distance between the detection element and a second frame body portion, which is brought into electrical contact with the second electrode terminal portion, is the same as the distance between the detection element and the other first frame body portion.

3. The sensor according to claim 1,
wherein, with a direction which is along the first main surface and the second main surface and which is orthogonal to the axial direction being defined as a width direction,
the other first electrode terminal portion and the second electrode terminal portion are disposed so as to overlap with each other in the width direction.

4. The sensor according to claim 1,
wherein a number of the first electrode terminal portions is larger than a number of the second electrode terminal portions.

5. The sensor according to claim 1,
wherein, with respect to the thickness direction of the detection element, a distance between the specific first frame body portion and the other first frame body portion is from 0.2 mm to 5 mm.

6. The sensor according to claim 1,
wherein, with respect to the axial direction, a distance between a contact portion between the specific first electrode terminal portion and the specific first frame body portion and a contact portion between the other first electrode terminal portion and the other first frame body portion is from 0.2 mm to 10 mm.

* * * * *